United States Patent [19]

Kleinerman

[11] Patent Number: 4,708,494

[45] Date of Patent: Nov. 24, 1987

[54] METHODS AND DEVICES FOR THE OPTICAL MEASUREMENT OF TEMPERATURE WITH LUMINESCENT MATERIALS

[76] Inventor: Marcos Kleinerman, 24 Jerome St., Southbridge, Mass. 01550

[21] Appl. No.: 608,932

[22] Filed: May 14, 1984

Related U.S. Application Data

[63] Continuation of Ser. No. 405,732, Aug. 6, 1982, abandoned.

[51] Int. Cl.[4] .................. G01J 05/58; G01K 11/12
[52] U.S. Cl. ........................ 374/161; 250/231 R; 250/458.1; 252/301.33
[58] Field of Search .............. 374/161, 162, 159, 121, 374/137; 250/458.1, 337, 231 R, 339, 461.2; 252/301.33; 356/44

[56] References Cited

U.S. PATENT DOCUMENTS

| | | | |
|---|---|---|---|
| 3,239,406 | 3/1966 | Coffman et al. | 250/361 C X |
| 3,639,765 | 2/1972 | Kleinerman | 250/330 |
| 3,996,472 | 12/1976 | Rabatin | 250/337 X |
| 4,061,578 | 12/1977 | Kleinerman | 250/330 |
| 4,075,493 | 2/1978 | Wickersheim | 374/159 |
| 4,136,566 | 1/1979 | Christensen | 250/227 X |
| 4,215,275 | 7/1980 | Wickersheim | 374/137 |
| 4,223,226 | 9/1980 | Quick et al. | 374/159 X |
| 4,245,507 | 1/1981 | Samulski | 250/337 X |
| 4,262,198 | 4/1981 | Gupta et al. | 250/340 |
| 4,278,349 | 7/1981 | Sander | 356/44 |
| 4,281,245 | 7/1981 | Brogardh et al. | 250/227 |
| 4,302,970 | 12/1981 | Snitzer et al. | 374/161 |
| 4,307,607 | 12/1981 | Saaski et al. | 374/161 |
| 4,313,057 | 1/1982 | Gelbwachs | 250/458.1 |
| 4,356,448 | 10/1982 | Brogardh et al. | 250/231 R X |
| 4,374,328 | 2/1983 | Tekippe et al. | 374/121 X |
| 4,376,890 | 3/1983 | Engstrom et al. | 250/461.1 |
| 4,409,476 | 10/1983 | Löggren et al. | 250/337 X |
| 4,437,772 | 3/1984 | Samulski | 374/159 X |
| 4,448,547 | 5/1984 | Wickersheim | 374/159 X |

OTHER PUBLICATIONS

Introduction to Solid State Physics by Charles Kittel, Nov. 1957, pp. 495, 496, 516, 517, 524.
McGraw-Hill Dictionary of Scientific and Technical Terms ©1978, p. 948, "Luminescent Center" defined.
"Optical Fibers with Reduced Pressure Sensitivity", N. Lagokos et al., May 5, 1981, Optics Letters, vol. 6, No. 9, Sep. 1981, pp. 443-445.
"A Temperature Measuring Device", E. Okamoto et al., Feb. 21, 1974, An Early Patent Application (Japanese Translated), No. 51452/72, pp. 3-8.

Primary Examiner—Daniel M. Yasich

[57] ABSTRACT

The present invention provides new methods and their associated materials and devices for the remote optical measurements of temperatures with luminescent sensors. These methods allow the use of a single sensor to measure temperatures over a wide range from the cryogenic regions to well above ambient temperatures, up to about 800 K depending on the sensor. Using fiber optic links a single, inexpensive light source, for example a light emitting diode, and a single photodetector are used to obtain normalized measurements from a sensor, only minimally affected by fluctuations in the intensity of the excitation light source, fiber and/or connector losses or detector drift. One preferred embodiment of this invention can be used with most luminescent materials and does not require a temperature-dependent change in the luminescence properties of the sensor within the temperature range being measured. Another preferred embodiment uses temperature-dependent luminescence decay times as temperature indicators, using a class of materials the luminescence quantum efficiency of which does not degrade within the temperature range being measured. The invention permits the use of a single sensor in two independent operative modes, thus providing redundancy and a self-checking feature.

22 Claims, 5 Drawing Figures

METHODS AND DEVICES FOR THE OPTICAL MEASUREMENT OF TEMPERATURE WITH LUMINESCENT MATERIALS

This application is a continuation of application Ser. No. 405,732, filed 8/06/82, now abandoned.

BACKGROUND OF THE INVENTION

1. Field of Invention:

The present invention relates to methods, materials and devices for the optical measurement of temperature, and more particularly, is directed towards new methods of using known luminescent materials for the optical measurement of temperature.

2. Description of the Prior Art:

Optical temperature sensors, namely sensors which convey temperature information in the form of optical signals, have been under development in recent years mainly in answer to a need in industry, medicine and scientific research to measure temperatures of objects and environments where the presence of electrical conductors is undesirable, such as, for instance, in the presence of microwaves or other oscillating fields. Often these sensors have been used in conjunction with optical fibers, whose function was to carry a probing light beam to the temperature sensor and to carry the optical signal produced by the sensor to a photodetector.

Another stimulus to the development of optical temperature sensors has been the growing need for sophisticated feedback and control devices in manufacturing, air and surfaces transportation, and environmental monitoring in large commercial and residential buildings. Optical sensors have an advantage over electrical sensors in that their signals can be transmitted with low attenuation, and without prior conversion or conditioning, over optical fibers, whose information-carrying capacity is greater and less subject to interference than that of electrical cables.

A further advantage of fiber optics temperature sensing systems is that they can be multiplexed so that a single light source and a single light detecting system can be used for measuring the outputs of many remote sensors simultaneously or quasi-simultaneously, with considerable cost savings over electrical sensing systems.

One of the earliest devices for the optical measurement of temperature used the temperature-dependent reflectivity of a liquid-crystalline material at the tip of a fiber bundle (Johnson, C. C. and Rozell, T. C., *Microwave Journal*, p. 55, August 1975). Other non-luminescent devices used the temperature-dependent light polarization of birefringent crystals (Cetas, T. C. and Connors, W. C., *Medical Physics* 5, 79 (1978)) and the temperature-dependent wavelength shift of the absorption edge of some semiconductors (Christensen, D. A., U.S. Pat. No. 4,136,566). All of these sensors have a relatively large thermal mass which make them unsuitable for sensitive radiometric measurements.

Only one optical temperature sensor, an indium phosphide semiconductor with a temperature-dependent absorption edge, has reportedly been uses for the measurement of cryogenic temperatures (NASA Technical Briefs, p. 55, August 1981). The procedure and instrument are relatively complicated, since a wavelength scan is required for each measurement in order to find the position of the absorption edge. As the method is not instantaneous, the system cannot be readily multiplexed for monitoring the outputs of a plurality of sensors.

Another optical method for temperature measurement makes use of temperature-dependent changes in the optical transmission of glass fibers doped with a rare earth ion having at least one electronic energy level close enough to the ground level to be thermally excited to a measurable extent (Baumbick, R. J. and Alexander, J., *Control Engineering*, March 1980, pp. 75–7). This level is optically coupled to higher energy levels with energy differences corresponding to specific optical wavelengths. An increase in temperature from $T_1$ to $T_2$ kelvins increases the occupancy number of lower, thermally excited level, by a factor approximately equal to $\exp[(E/k)(T_1^{-1}-T_2^{-1})]$, where E is the energy of said thermally excited level, relative to the ground level, and k is the Boltzmann constant. This results in a decreased transmission of light of said specific wavelengths. The method is suitable for measuring relatively high temperatures, such as those of the exhaust gases from aircraft engines.

Measurements of light transmission through optical temperature sensors are subject to error, especially in fiber optic systems, as changes in the optical signals caused by variable optical losses of fibers, connectors and/or couplers may be confused with the temperature-dependent signals. Techniques for minimizing such errors are relatively complex, and have included the use of a second light source to generate a reference light beam of a wavelength not subject to a temperature-dependent absorption by the sensor (Kyuma et. al., *IEEE J. Quant. Electron.*, QE-18(4), 667 (1982)). Even then, a serious source of error remains, namely the intensity fluctuations of one or both light sources.

The use of luminescent sensors offers the advantage that the sensor itself is the second light source, which generates a resolvable luminescence light the intensity of which is proportional to the excitation light intensity absorbed by the sensor. By dividing the signal from the sensor luminescence by that from the excitation light beam transmitted through the sensor, one can essentially eliminate not only the effect of the fluctuations of the intensity of the excitation light, but also that from the optical losses in the fiber optic system. In addition to permitting the use of simpler measuring devices, luminescence techniques are more sensitive at low optical densities. Therefore, it is desirable to have sensitive luminescence methods for optical temperature measurement, preferably operable at wavelengths which are transmitted through fiber optic systems with low attenuation.

U.S. Pat. Nos. 3,639,765 and 4,061,578 describe methods for measuring infrared radiation by means of phosphors, including europium-doped terbium chelates, having a very low thermal mass and two non-overlapping luminescence spectral bands, the intensity ratio of which is a unique function of temperature, independent of intensity changes of the excitation light. The infrared radiation is absorbed by a thin black film whose temperature is increased according to the amount of infrared radiation absorbed. The temperature rise in the film is measured by a thin layer of the phosphor in thermal contact with said black film. In contrast to the other optical temperature sensors described above, the class of europium-doped terbium chelates can be used both as contact sensors and as sensitive radiometric sensors, and can measure contact temperatures over a wide range from near absolute zero to about 400 kelvins.

U.S. Pat. Nos. 4,075,493 and 4,215,275 describe inorganic europium-doped oxysulfides of lanthanum, gadolinium and yttrium as luminescent temperature sensors. Like the europium-doped terbium chelates mentioned above, these phosphors are characterized by emitting luminescence in at least two non-overlapping spectral bands the intensity ratio of which is a known function of temperature. These inorganic phosphors have a lower luminescence excitation efficiency and a much larger thermal mass than the europium-doped chelates, and cannot operate at cryogenic temperatures. They are, however, more stable at temperatures above 400 kelvins than the chelates.

Both the europium-doped oxysulfides and the europium-doped terbium require excitation with ultraviolet or violet light. This limits the distance over which the excitation light can be transmitted over optical fibers, as the corresponding wavelengths are more strongly attenuated than red or near infrared wavelengths.

A recently disclosed method for the optical measurement of temperature uses AC-modulated blue light to excite the luminescence of samarium (III) in a crystalline barium fluoride chloride host (McCormack, J. S. *Electronics Letters* 17, 630 (1981). The sensor temperature is determined from the decay time of the luminescence, said decay time, as well as the luminescence efficiency, decreasing with increasing temperature. The method has relatively low sensitivity and accuracy, and the need to use blue excitation light restricts the use of the method to relatively short transmission distances.

The current needs in the area of optical temperature sensing are: (a) new sensors for the successful implementation of new or previously disclosed methods for temperature measurement, and (b) improved methods for the accurate measurement of temperature, useful for wide temperature ranges, and implementable with optical wavelengths transmittable over long lengths of optical fibers with relatively little attenuation.

It is one object of the present invention to provide new luminescence methods and associated devices for the remote optical measurement of temperature, from the cryogenic region to over 800 kelvins. These methods are implementable, either throughout the whole or in portions of this wide range, with any solid or liquid luminescent material composed of molecules the electronic ground level of which comprises vibrational sublevels. This class of materials comprises most known luminescent materials.

It is another object of the present invention to provide new luminescent materials as sensors for the optical measurement of temperatures and spatial temperature distributions.

Other objects of the present invention will become apparent from the following description.

The invention accordingly comprises the methods, materials, apparatuses and systems, together with their steps, part, elements and interrelationships that are exemplified in the following disclosure, the scope of which will be indicated in the appended claims.

SUMMARY OF THE INVENTION

The objects of this invention are accomplished by the use of two distinct technologies, both using luminescent probes and both based on the measurement of a thermal equilibrium between the occupancy numbers of two molecular energy levels of a luminescent material used as a temperature probe. In each of these two technologies, described in greater detail hereinafter, the measured quantity is determined by the value of the Boltzmann factor $\exp(-E/kT)$, where E ($E_v$ in one case and E' in the other) is the energy difference between the two levels, k is the Boltzmann factor and T is the absolute temperature of the probe.

In the first technology one measures the temperature-dependent absorption coefficient of a luminescent probe by generating therein a luminescence light emission the intensity of which is proportional to the temperature-dependent fraction of the intensity of the interrogating light which is absorbed by the probe. This method provides not only a direct measurement of said absorbed fraction (in contrast to the conventional method in which the absorbed light intensity is determined *indirectly* from the difference between the intensities of the incident light and the transmitted light) but it also provides two separable optical signals, namely the luminescence light intensity, proportional to the intensity of the absorbed light, and the intensity of the transmitted (non-absorbed) interrogating light. The ratio of these intensities is an accurate indicator of the probe temperature, unaffected or only minimally affected by fluctuations of the intensity of the interrogating light source or light losses in the optical system. In contrast to *all* the prior art methods which use luminescent probes, this method can be used with most solid, or liquid luminescent materials and, since it monitors an absorption process (occurring *before* any luminescence emission), it does not require or involve any temperature-dependent change in the luminescence properties of the probe material.

In the second technology one measures a temperature-dependent process which occurs *after* the absorption of light in a luminescent material the luminescence quantum efficiency of which remains essentially constant over the temperature range of operation of the measuring device.

Although the physical processes on which the above two technologies are based are independent of each other, there is an important link between them related to the teachings of this invention: These otherwise mutually independent physical processes can be made to take place in the same probe, activated by the same light source and measured by the same photo-detection system. Since these processes are physically independent of each other, the temperature measurements based on either of them can be used to check the temperature readings obtained from the other. A single thermometric device using both of these two technologies will then be a self-checking device. A self-checking capability is very valuable for an ever-increasing number of applications where an instrumental malfunction must be immediately detected, lest disastrous consequences could ensue, as in the operation of nuclear power plants or in airplane navigation systems.

DEFINITIONS

Some of the terms used in this application often have different meanings in different contexts. Within the context of this application I am using the following definitions:

Light: optical radiation, whether or not visible.

Luminescent centers: the molecules of ions of the luminescent material which can absorb the illuminating light (also referred to as 'interrogating light') and convert this absorbed illuminating light into luminescence light emitted at wavelengths different from those of the absorbed light.

Radiationless process: a process which is not accompanied by the absorption or emission of light.

Occupancy number of an energy level: the fraction of the luminescent centers of the sensor material occupying said energy level.

Vibronic material: any material whose molecular electronic ground energy level comprises a plurality of vibrational sublevels with energies higher than that of the lowest occupied level of the material, said vibrational sublevels being so distributed as to cover an essentially continuous wide band of energies.

Vibronic level: a vibrational sublevel of the electronic ground level (also referred to as 'ground state') of the vibronic material, having an occupancy number which increases with increasing temperature according to the value of the value of the Boltzmann factor, $\exp(-E_v/kT)$, where $E_v$ is the energy of said vibrational sublevel relative to the lowest occupied level of the material, k is the Boltzmann constant and T is the absolute temperature of the material in kelvins.

BRIEF DESCRIPTION OF THE DRAWINGS

A fuller understanding of the nature and objects of the present invention will become apparent upon consideration of the following detailed description taken in connection with the accompanying drawings.

DESCRIPTION OF THE PREFERRED EMBODIMENTS

Figure 1:
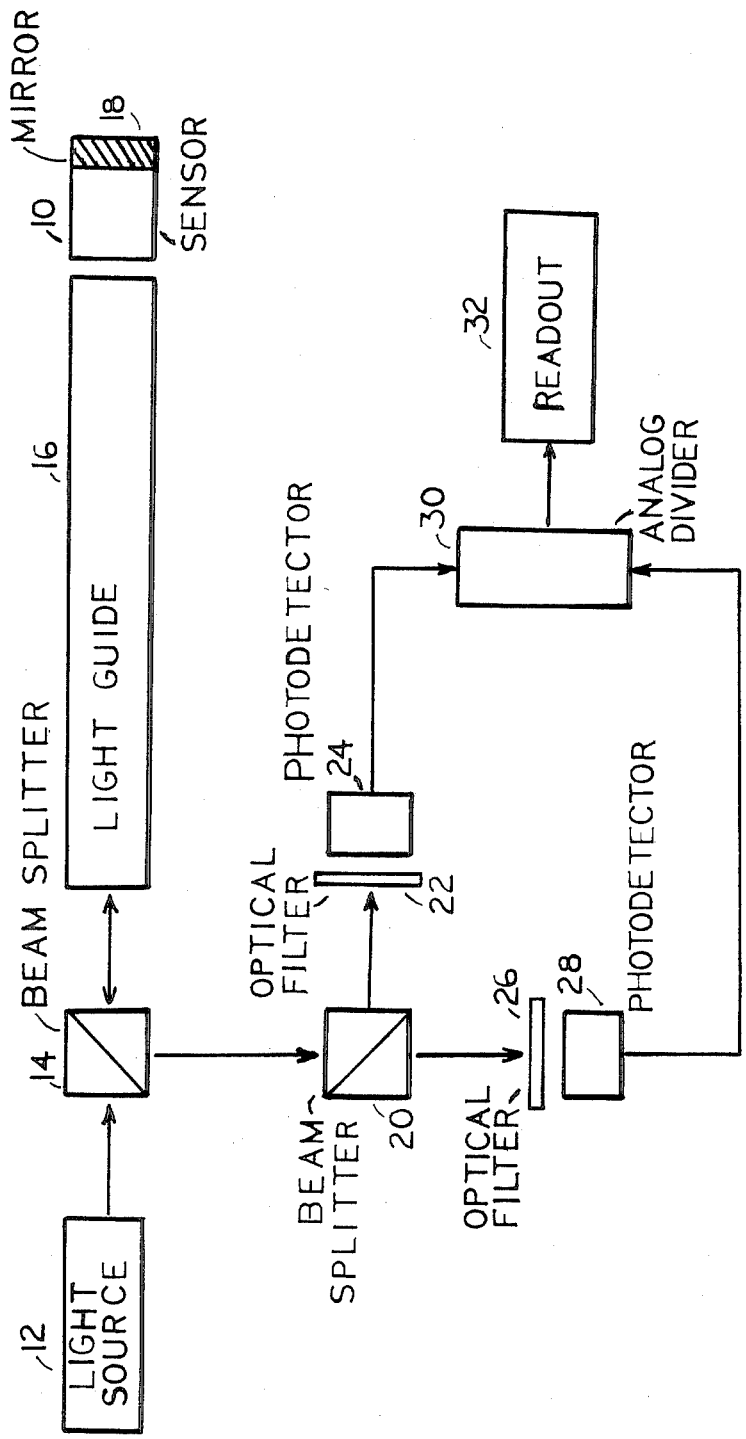
FIG. 1 is a schematic diagram of a temperature-measuring system embodying the invention.

FIG. 1 is a schematic representation of an embodiment of a system of optical thermometry which includes some basic features of the present invention. The environment 1 whose temperature is being measured is placed in a heat flow relationship with a temperature sensor 10, said sensor consisting of one of the luminescent materials disclosed hereinafter, characterized by a temperature-dependent absorption coefficient when excited with light within a defined spectral region, said light being produced by light source 12. This excitation light is directed to sensor 10 through the dichroic beam splitter 14 and the light-carrying assembly 16. The beam splitter 14 is characterized by transmitting most of the excitation light incident on it and by reflecting most of the luminescent light emitted by the sensor. The light-carrying assembly 16 contains at least one optical element, for instance a lens or, preferably, a fiber optics light guide, the functions of which are to conduct the excitation light to sensor 10 and to collect at least part of the luminescence light generated at said sensor. This luminescence light, together with the fraction of the excitation light transmitted by the sensor and reflected back by mirror 18, is directed to beam splitter 14, where it is reflected toward the dichroic beam splitter 20, which separates the luminescence light from the excitation light transmitted by the sensor. The intensity of the luminescence light beam, filtered by optical filter 22, is measure by photodetector 24, and the intensity of the transmitted excitation light, filtered by optical filter 26, is measured by photodetector 28. The photosignals from detectors 24 and 28 are ratioed at the electronic divider 30. The resulting ratio is a unique function of temperature for a given sensor, independent of any change in the light source output. The sensor temperature, which is also the temperature of environment 1, is displayed at the readout device 32.

A similar embodiment to that shown in FIG. 1 is used when the luminescent material, chosen from the group of materials disclosed hereinafter, absorbs the excitation light to an extent which may or may not vary with temperature, and emits luminescence light having at least two spectral components the intensity ratio of which is a known function of temperature. In this case the optical system is modified so that said two spectral components are collected, separated and measured each by a different photodetector. The detector signals are ratioed as in the embodiment of FIG. 1, and the resulting ratio is an indicator of the temperature of the object or environment being measured.

Figure 5:
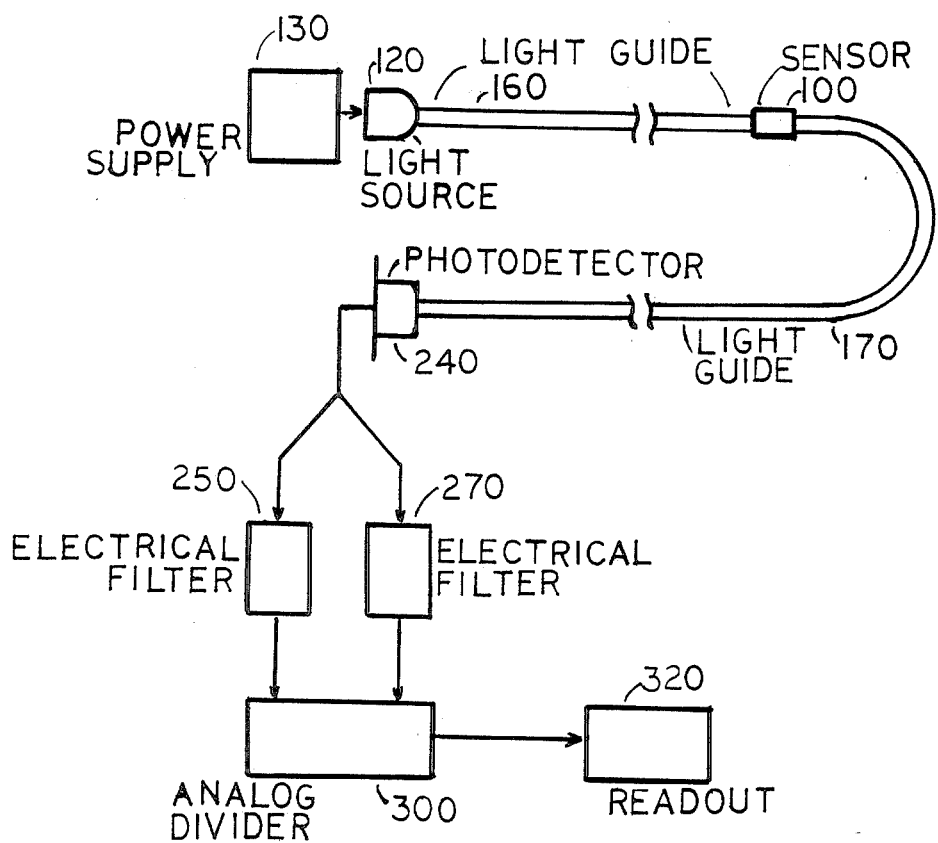
FIG. 5 is a schematic diagram of a simple device for the optical measurement of temperature according to this invention.

In another embodiment, described in greater detail in the section entitled "Self-checking features of the disclosed embodiments" and illustrated in FIG. 5, the sensor, characterized by a temperature-dependent absorption coefficient and a luminescence decay time of the of the order of $10^{-5}$ seconds or longer, is excited with pulsed or AC-modulated light the intensity of which decays in a time much shorter than the luminescence decay time of the sensor. Both the excitation light transmitted by the sensor and the luminescence light emitted by it are directed to a single photodetector. The two electrical signals generated therein have different time dependences, and are separated by electrical frequency filter, measured and ratioed to give an indication of the sensor temperature. An important advantage of this embodiment is that the measured ratio is unaffected by drifts in detector sensitivity or noise, in addition to being unaffected (or only minimally affected) by fluctuations of the intensity of the interrogating light source or fiber and/or connector losses.

PREFERRED SENSOR MATERIALS AND THEIR CHARACTERISTICS

Vibronic materials

Luminescent vibronic materials, the light absorption of which varies as a known function of temperature when excited within a defined spectral region, are a preferred class of sensor materials for the practice of this invention. Methods for using said materials as temperature sensors are explained in the following paragraphs.

Figure 2:
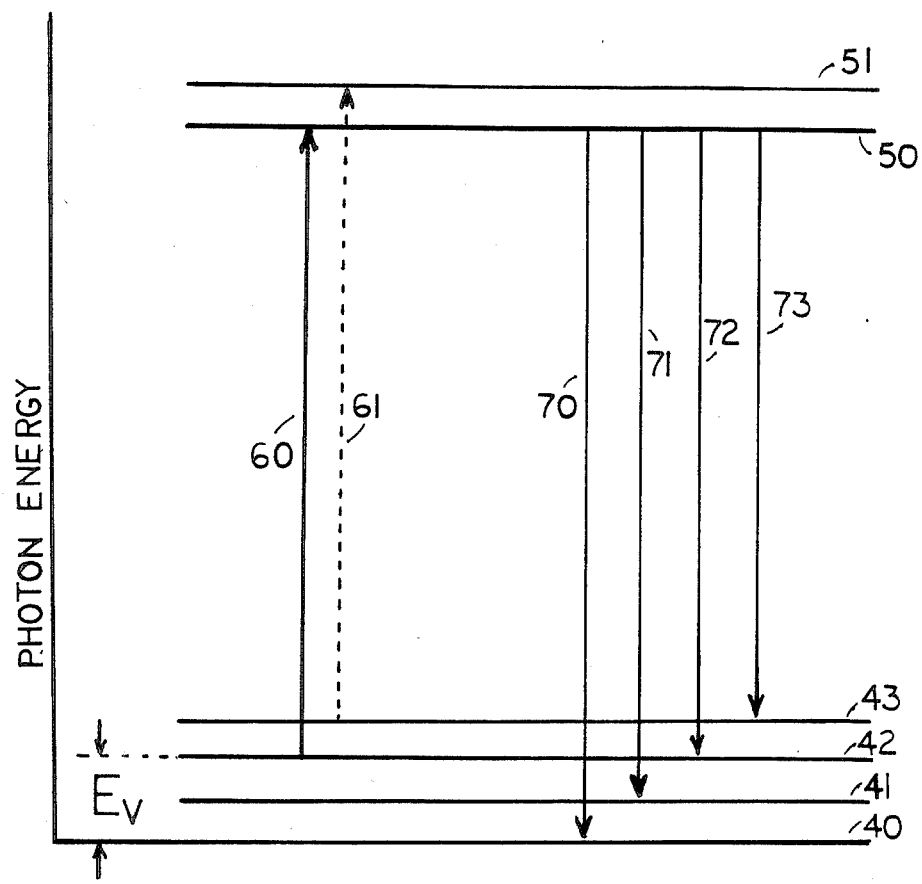
FIG. 2 is a simplified molecular energy diagram illustrating a temperature-dependent absorption process in a luminescent vibronic material used in this invention when excited with light of a suitable, predetermined photon energy, followed by luminescence emission.

FIG. 2 is a simplified representation of the processes which control the operation of the temperature sensors of this invention based on luminescent vibronic material. Although actual systems are generally more complicated, the model of FIG. 2 is valid for the limited purpose of explaining the basic phenomena underlying the operation of these sensors, and the temperature dependence of the optical signals actually observed in real systems follows essentially the predictions based on this model and the relevant equations which are presented below.

Referring to FIG. 2, the ground electronic level of the vibronic material comprises vibronic levels 40, 41, 42, 43 and other levels which, for the sake of simplicity, are not shown. The excited electronic level comprises vibrational sublevels 50, 51 and other vibrational sublevels not shown. The vertical arrowed line 60 represents an optical electronic transition produced by the absorbed excitation light, from level 42 to vibrational sublevel 50, which has an energy $E_s$ relative to level 40. The length of line 60 corresponds to the photon energy of the optical transition and, hence, to the specific wavelength $\lambda_e$ of the excitation light. This wavelength obeys the relation $\lambda_e = hc/(E_s - E_v)$, where h is Planck's constant and c is the velocity of light in a vacuum. The wavelength $\lambda_e$ can excite only molecules occupying vibronic level 42 and, to a smaller extent, molecules occupying slightly higher levels, the excitation of which is represented by the dotted vertical line 61. Luminescence emission occurs from sublevels 50 to the vibronic levels of the ground electronic level, said emission represented by lines 70, 71, 72 and 73. As shown in FIG. 2, a considerable spectral portion of the emission occurs at photon energies higher than that of the excitation light, and is commonly referred to as anti-Stokes luminescence.

In practice the vibronic material is often used as a solid solution, glassy or crystalline, in a transparent host material, said solid solution constituting the temperature sensor. The concentration of the vibronic material and the dimensions of the sensor are chosen so that the sensor absorbs only a fraction $\alpha_v$ of the nearly monochromatic excitation light within the temperature range of operation, and transmits the rest. The absorbed fraction obeys the following relation $$\alpha_v = 1 - 10^{-\epsilon c_o d(N_{42}/N)} \quad (1)$$

where
$\epsilon$ is the molar decadic absorption coefficient of the molecules occupying vibronic level 42;
$c_o$ is the total molar concentration of the vibronic material;
d is the length of the sensor in the direction of the incident excitation light;
$N_{42}$ is the number of molecules of the vibronic material occupying vibronic level 42; and
N is the total number of molecules of the vibronic material.

The ratio $N_{42}/N$ essentially follows the relation $$N_{42}/N = f^{-1} \cdot \exp(-E_v/kT) \quad (2)$$

where f is the partition function of the luminescent molecular system.

The expression $c_o \cdot f^{-1} \exp(-E_v/kT)$ is essentially the effective molar concentration of the molecules of the vibronic material occupying vibronic level 42.

The quantity $10^{-\epsilon c_o d(N_{42}/N)}$ represents the fraction of the intensity of the illuminating light (excitation light) which is transmitted by the sensor. In the absence of scattering and/or reflection losses (as assumed herein for didactic purposes), it is equal to $(1 - \alpha_v)$.

At optical densities no greater than about 0.02, $\alpha_v$ is essentially given by $$\alpha_v = 2.3 \epsilon c_o d f^{-1} \exp(-E_v/kT) \quad (3)$$

At optical densities greater than 0.02 the relationship between $\alpha_v$ and the Boltzmann factor $\exp(-E_v/kT)$ becomes less linear, but the validity of equations (1) and (2) is not affected, and the method can be used at high or low optical densities.

The luminescence intensity I obeys the relation $$I = P_o(\lambda_e/hc)\alpha_v\phi \text{ photons} \cdot \sec^{-1} \quad (4)$$

where $P_o$ is the radiant power of the incident excitation light, and $\phi$ is the luminescence quantum efficiency of the material.

Sensors made from materials having high $\phi$ values can produce large signal-to-noise ratios even with optical densities lower than 0.01, provided that the optical system has at least a moderately high collection efficiency for the generated luminescence. Such efficiency is easily obtainable with state-of-the-art fiber optic systems.

The sum of the light intensity absorbed and the light intensity transmitted by a clear medium is essentially constant. It follows, then, that as the absorbed fraction $\alpha_v$ increases with an increase in temperature according to equation (3), the intensity of the transmitted fraction must decrease accordingly. Since, according to equation (4), the intensity of the luminescence light is directly proportional to $\alpha_v$, it follows that the ratio of the intensity of the luminescence light to that of the transmitted light increases with an increase in temperature, and the ratio can be used as a temperature indicator.

The temperature coefficient of the luminescence intensity follows approximately the relation $$(1/I_o)(dI/dT) = E_v/kT^2 \quad (5)$$

where $I_o$ is the luminescence intensity at a chosen reference temperature. For example, a material with a value of $E_v$ of 1800 cm$^{-1}$ has a coefficient close to three per cent per kelvin at a temperature of 295 K.

Equation (4) shows that the method of the preceding paragraphs requires only a temperature-dependent change in the absorption coefficient of the sensor material at wavelengths corresponding to photon energies lower than the energy $E_s$ of the excited level. This property is shared by virtually all solid and liquid luminescent materials. The method does not require any temperature-dependent changes in the luminescence quantum efficiency, spectral distribution or decay time. Therefore, and in contrast to all prior art methods, it can be implemented with most luminescent materials.

An important advantage of the vibronic materials of this invention, with respect to their use as temperature sensors, is that the value of $E_v$, which determines the optimum temperature range of operation, can be chosen and varied at will over a continuum of values simply by choosing, for any given material, the photon energy of the excitation light relative to the energy $E_s$ of the excited emissive level (sublevel 50 in FIG. 2). Thus, a single sensor can be used for measuring temperature over a wide range from cryogenic temperatures up to the highest temperatures which the sensor can withstand without deterioration. An additional advantage derives from the fact that there are many luminescent vibronic materials having absorption and luminescence spectra over a wide spectral region from the ultraviolet to the near infrared. One can choose, therefore, the wavelength region most suitable to one's needs. For instance, if it is required to transmit the optical signal over long distances via an optical fiber, one could choose a material with absorption and luminescence bands at wavelengths longer than 700 nanometers (nm).

In a preferred embodiment, one measures the ratio R of the luminescence intensity I to the intensity of the illuminating light transmitted (non-absorbed) by the sensor. In a clear medium, the fraction of the intensity of the illuminating (excitation) light which is transmitted by the sensor is, of course, equal to $(1-\alpha_\nu)$. Since the luminescence intensity I is proportional, to $\alpha_\nu$, it follows that R obeys the relation $$R = A\left[\frac{\alpha_\nu}{1-\alpha_\nu}\right]$$

which at low optical densities becomes $$R = \left[\frac{\exp(-E_\nu/kT)}{1-\exp(-E_\nu/kT)}\right] A \qquad (5A)$$

where A is a constant.

In addition to the advantage of allowing ratiometric measurements using a single, narrow band excitation light source (for instance, an inexpensive laser diode) and a single photodetector, the direct measurement of a temperature-dependant intensity of absorbed light by luminescence means has the additional advantage, compared to the measurement of a temperature-dependent transmitted light intensity, that the temperature coefficient of the generated luminescence intensity I is, at low optical densities, orders of magnitude greater than the temperature coefficient of the transmitted light intensity, thus allowing more accurate measurements with simpler equipment. An example follows. Suppose that $\alpha$ is equal to 0.01 to 300 K., and that the value of $(E_\nu/k)$ is 1500 deg$^{-1}$. From equation (5), the value of I increases by 1.67 percent per degree change near 300 K. The intensity of the transmitted light, however, increases only by 0.017 percent, which is difficult to measure with simple equipment, compared to the relatively easy measurement of a 1.67 percent change.

In one example the sensor is a solution of an oxazine dye in a solid plastic. The dye has an emissive level with an energy of about $1.5 \times 10^4$ cm$^{-1}$. The concentration of the dye is adjusted so that a sensor having a length d of 0.5 cm has an optical density of 0.01 when illuminated with light of a wavelength $\lambda_e$ of $7.6 \times 10^{-5}$ cm, generated by an aluminium gallium arsenide laser, with a radiant power of 3 milliwatts. The corresponding value of $E_\nu$ is approximately 1800 cm$^{-1}$. The fluorescence quantum efficiency of the dye within the temperature range of operation is 0.7. Two and one half percent of the total fluorescence intensity emitted by the dye reaches the photodetector. Under these conditions, the fluorescence radiant power reaching the photodetector is approximately equal to $1.2 \times 10^{-6}$ watts. At temperatures near 300 K., a temperature change of only 0.1 K. produces a signal reaching the photodetector of about $3.5 \times 10^{-9}$ watts. This is several orders of magnitude greater than the equivalent noise in typical silicon photodetectors. Because of the large signals thus obtainable, a sensing system can be multiplexed so that many sensors in different locations can be monitored simultaneously or quasi-simultaneously with a single light source and a single detection unit.

In another example of a temperature-measuring system according to this invention, the sensor is a crystal of emerald. This material, also operative in the 700 to 900 nm region, can be used over a wide temperature range from below ambient to over 800 K. In general, inorganic materials, of which emerald is an example, are preferred over organic materials for use at temperatures much higher than 400 K. The luminescent centers in emerald are chromium(III) ions. Other inorganic crystals doped with chromium(III) or other transition metal ions like Nickel(II), cobalt(II) or vanadium(II) are also suitable for the practice of this invention.

Figure 3:
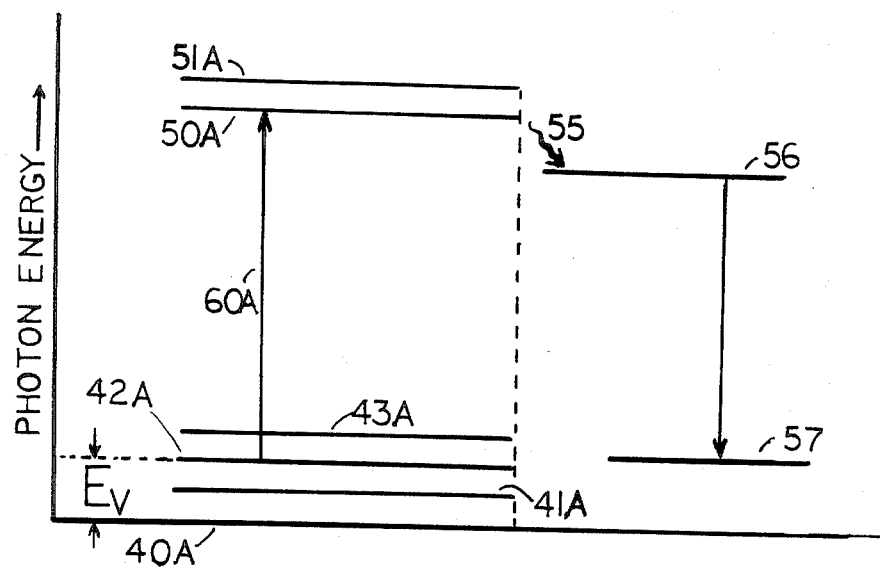
FIG. 3 is a simplified molecular energy diagram illustrating a similar temperature-dependent absorption process to that of FIG. 2, but followed by a different process of luminescence emission.

Another class of vibronic materials also suitable for use as temperature sensors according to this invention are described with reference to FIG. 3, which shows an energy 'flow sheet' at the molecular level. Excitation of molecules occupying a vibronic level proceeds in the same manner as shown in FIG. 2 for the materials described hereinbefore. Levels 40A, 41A, 42A, 43A, 50A and 51A are similar to levels 40, 41, 42, 43, 50 and 51, respectively. The same digits in both figures indicate the similarity of the excitation processes, and the A's were added to the levels of FIG. 3 to indicate that these levels belong to a different class of vibronic materials. The difference is that in this class the optically excited level 50A transfers at least a major part of its excitation energy, via a radiationless decay represented by the wavy line 55, to the lower level 56, of the same or a different molecular species. Luminescence emission occurs from level 56 to a lower level 57 or to any other lower-lying levels which may or may not include any of the levels 40A, 41A, 42A or 43A. Examples of this class of vibronic materials include virtually all phosphorescent organic dyes, luminescent chelates of terbium(III) and europium(KII), and some solid solutions of inorganic vibronic materials co-doped with other luminescent centers. Examples of the latter are crystalline or glassy materials co-doped with chromium(III) and neodymium(III) ions, in which chromium(III) absorbs the excitation light and sensitizes the luminescence from neodymium(III).

Two other clases of materials suitable for the practice of this invention are: (a) luminescent lanthanide ions dissolved at relatively high concentrations in crystalline or glassy hosts, and having at least one electronic energy level which can be thermally populated to a measurable extent at the temperatures being measured, and (b) luminescent semiconductors with a temperature-dependent absorption edge wavelength. Both classes of materials are characterized by an absorption coefficient which, within a relatively narrow spectral region, increases exponentially with increasing temperature in essentially the same manner as with the vibronic materials described hereinbefore. Therefore, they are used in the same manner and with the same methods as discussed above.

In the above-described embodiments the luminescent centers had a temperature-dependent absorption coefficient to light of photon energy lower than that of the electronic level being excited. These centers are designated herein as A centers. One preferred procedure for referencing the signals from these centers is to incorporate in the same medium other luminescent centers, designated herein as B centers, the absorption coefficient and luminescence intensity of which are approximately independent of temperature within the temperature range being measured, when excited with light of the same wavelength as the A centers, and the luminescence of which is emitted in a spectral region different from that of the A centers. In one divides the luminescence intensity emitted by the A centers by the luminescence intensity emitted by the B centers, the ratio so obtained is a unique function of temperature. An example of such a sensor consists of a transparent acrylic or epoxy polymer co-doped with a high concentration of the europium(III) chelate Eu(TTA)Phen and a small concentration of the fluorescent dye CI Solvent Yellow 44, wherein TTA represents the anion of the ligand 4,4,4Trifluoro(2-thienyl)-1,3-butanedione, Phen represents 1,10-phenanthroline, and the dye CI Solvent Yellow 44 has the following structure

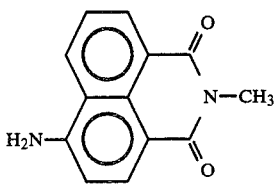

When excited with the 436 nm line from a small mercury arc lamp, the absorption coefficient of Eu(TTA)-Phen increases with increasing temperature, with a corresponding increase in its luminescence intensity, in accordance with equations (3) and (4). The main luminescence band of the chelate is at 612 nm, and the described behavior occurs within a temperature range below the onset of thermal quenching of the chelate luminescence. The absorption coefficient of CI Solvent Yellow 44 is essentially invariant within said temperature range, and its fluorescence peaks at about 535 nm. The chelate molecules are the A centers, and the molecules of Solvent Yellow 44 are the B centers. The intensity ratio of the luminescence emissions from said two kinds of centers is an indicator of the sensor temperature. Said ratio can be obtained by separating, by means of optical filters, the emission bands from each of said two kinds of centers, and directing each separated band to a separate photodetector, the two electrical signals thus generated being fed to an electronic divider. Alternatively, the excitation light is fully AC-modulated at about $2 \times 10^4$ Hz, and the luminescence from both kinds of centers is directed to a single photodetector. The electrical signal produced by the fluorescence from the yellow dye has the same AC frequency as the AC-modulated excitation light, but the chelate luminescence is DC, as its long decay time, of the order of $10^{-3}$ seconds, cannot follow the oscillations of the excitation light. The AC and the DC signals are separated by standard techniques, and their ratio is then measured by an electronic divider.

Materials for the measurement of spatial temperature distributions

It is often necessary to accurately measure spatial temperature distributions, whether on two-dimensional surfaces or on irregularly shaped objects. A sensor which could be coated on the the measured object as a film emitting a temperature-dependent luminescence should allow such measurements to be made. Luminescent materials having such capabilities have been disclosed in a scientific publication (Kleinerman, M., *Applied Optics,* 10, 825 (1971) and in U.S. Pat. Nos. 3,639,765 and 4,061,578. These three references disclose a thin film of a luminescent material coated on a black layer having an inhomogeneous microscopic temperature distribution, said distribution produced by the absorption of different intensities of thermal infrared radiation by different parts of the black layer. The luminescent film disclosed in said three references consisted of crystalline europium-doped terbium chelates characterized by emitting, when excited by ultraviolet or violet light, visible luminescence in two non-overlapping bands the relative intensities of which are a known function of temperature. Such materials can be applied to any object, large or small, the surfaces of which may have an inhomogeneous temperature distribution. An important application is the measurement of thermal profiles of integrated electrical circuits during operation, aimed at the detection of circuit flaws by observing any deviations from the expected normal thermal profile. Another important application is the measurement of laser beam powers and/or energies, and laser beam intensity profiles. New luminescent materials disclosed herein, suitable for these and similar applications, include the chelates $Tb(Diket)_3.Phen$, $Tb(Diket)_3.Bip$, $Tb(Diket)_3\phi_2Phen$, $Tb(Diket)_4.Q$, and each of the above terbium chelates doped with a small concentration of the europium chelate having the same organic ligands, wherein Diket represents a $\beta$-diketone chosen from the group comprising 4,4,4-Trifluoro-1-phenyl-1,3-butanedione,
4,4,4-Trifluoro-1-(p-diphenyl)-1,3-butanedione,
4,4,4-Trifluoro-1-(2-thienyl)-1,3-butanedione,
4,4,4-Trifluoro-1-(3-pyridyl)-1,3-butanedione,
4,4,4-Trifluoro-1-(2-furyl)-1,3-butanedione,
1,3-Diphenyl-1,3-propanedione
1-(p-diphenyl)-3-phenyl-1,3-propanedione,
1-Phenyl-1,3-butanedione,
1-(2-furyl)-1,3-butanedione,
1,3-bis-(p-diphenyl)-1,3-propanedione, and
1,3-bis-(p-methoxyphenyl)-1,3-propanedione;

Phen represents 1,10-Phenanthroline,
Bip represents 2,2'-Bipyridine,
$\phi_2$Phen represents 4,7-Diphenyl-1,10-Phenanthroline, and
Q represents a quaternary ammonium compound derived from the group of tertiary amines comprising pyridine, piperidine, morpholine, pyrazine, piperazine and tris(alkyl)amine, where alkyl represents any saturated hydrocarbon radical with up to eight carbon atoms.

The above chelates can be used either as point indicators, or in paints, films or attached sheets as indicators of spatial temperature distributions.

Other luminescent materials of this invention which are useful for the measurement of spatial temperture distributions, including the mapping of microscopic temperature profiles on current-carrying intefrated circuits, consist of inorganic semiconductor films doped with luminescent centers characterized by emitting, when excited with light of suitable wavelength, at least two spectrally resolvable luminescence bands, the intensity ratio of which is a known function of temperature. In one example, an integrated circuit chip, already coated with a very thin insulating inorganic film, is coated by techniques known in the art with a thin film of gallium phosphide doped with zinc and oxygen atoms. When excited with light of wavelengths shorter than 530 nm, said film emits luminescence in two non-overlapping bands peaking at 696 and 911 nm, respectively. The ratio of the intensity of the long wavelength band to that of the shorter wavelength band increases markedly with an increase in temperature. A preferred method for obtaining and displaying the temperature distribution on the chip surface is by scanning its surface with a flying spot scanner, as illustrated in U.S. Pat. No. 4,061,578, the teachings of which are incorporated herein by reference. With said method, the spatial resolution is determined both by the thickness of the coating and by the wavelength of the flying spot. The latter is made as short as necessary. Spatial resolutions much shorter than one micrometer are obtained, for example, with excitation wavelengths in the ultraviolet region. Circuits with components smaller than visible wavelengths and coated with similarly thin luminescent layers are scanned with short wavelength electron beams, for resolving spot sizes much smaller than the luminescence wavelengths.

Luminescent materials with two emissive levels in thermal equilibrium

Figure 4:
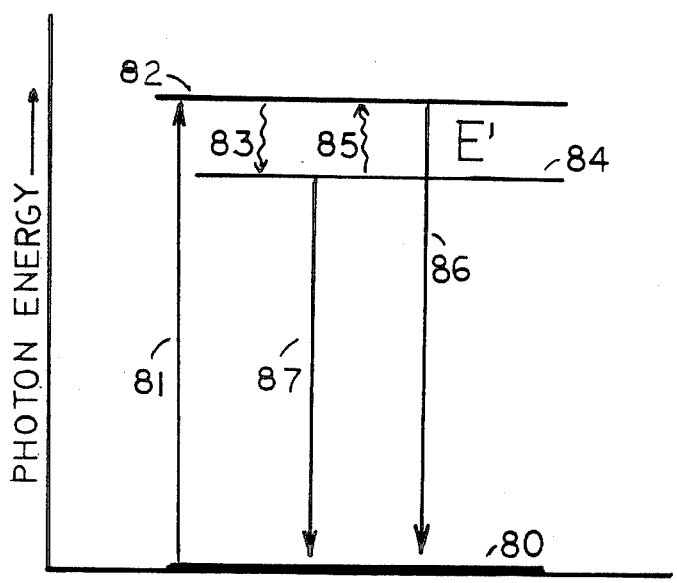
FIG. 4 is a schematic illustration of a temperature-dependent luminescence process determined by the thermal equilibrium between the occupancy numbers of two emissive energy levels of the sensor material.

One of the methods of this invention for the optical measurement of temperature uses the properties of a class of materials characterized by having a Boltzmann equilibrium between the occupancy numbers of two excited emissive levels, the relative contributions of which to the total luminescence intensity vary as a known function of temperature. In contract to the materials disclosed in U.S. Pat. Nos. 3,639,765, 4,061,578, 4,075,493, and 4,215,275, which are characterized by a decrease in the luminescence in the luminescence intensity of the higher of two emissive levels with increasing temperature, the luminescence from the higher level in the materials of this invention becomes more intense with an increase in temperature. The processes responsible for this intensification are illustrated in FIG. 4, to which the following description applies. Molecules or ions of the luminescent material occupying the ground electronic level 80 are excited by absorption of light, as depicted by arrowed line 81, to the emissive level 82, from which they decay rapidly, via the radiationless process 83, to the long-lived excited emissive level 84. A fraction of the molecules or ions occupying level 84 are thermally excited, via radiationless step 85, to emissive level 82, the occupancy number of which, relative to level 84, follows approximately the relation, in absence of level degeneracy, $$(N_{82})/(N_{84}) = \exp(-E'/kT) \quad (6)$$

where $N_{82}$ and $N_{84}$ are the occupancy numbers of levels 82 and 84, respectively. k is the Boltzmann constant and E' is the energy difference between these two levels. Levels 82 and 84 emit luminescence via radiative decays 86 and 87, with radiative rate constants $k_r$ and $k_r'$, respectively, with $k_r' >> k_r$. The ratio R' of the luminescence intensity from level 82 to that from level 84 follows approximately the relation $$R' = k_r'(N_{82})/k_r(N_{84}) \quad (7)$$

which can also be written as $$R' = (k_r'/k_r)\exp(-E'/kT) \quad (8)$$

Equation (8) shows that R' increases exponentially with increasing temperature. The value of R' can be measured by comparing the spectrally resolved luminescence intensities from each of the two emissive levels or, often more conveniently, by measuring the decay time $\tau$ of the total luminescence from the two levels. This decay time decreases with increasing temperature according to the relation $$\tau = \frac{[1 - \exp(-E'/kT)]}{[k_r + k_r'\exp(-E'/kT)]} \text{ seconds} \quad (9)$$

A measurement of $\tau$ gives, therefore, an indication of the sensor temperature. The preceding treatment is applicable when the excitation light generates luminescence from only one kind of emissive center in the sensor. If this condition is not met the luminescence response deviates somewhat from the predictions of the preceding equations. Such deviations do not affect the usefulness of this method of temperature measurement. In practice the sensor is calibrated by recording a $\tau$ v. temperature curve within the desired temperature range, with the aid of a precision reference thermometer, and storing said information in an electronic memory. Measurements made afterwards with the luminescent sensor are compared automatically with the stored information by means of a microprocessor and/or other inexpensive electronic components, and the measured decay times are thus converted into reliable temperature readings. Examples of sensors useful with this method are crystals of aluminium oxide, beryls, magnesium oxide and garnets, doped with chromium(III) or vanadium(II).

It follows from equations (6) to (9) that this method for measuring temperature does not require any change in the total luminescence quantum efficiency of the sensor material, in contrast to all prior art methods based on temperature-dependent luminescence decay times, which involve a decrease of the quantum efficiency with increasing temperature. Furthermore, as this method depends only on a Boltzmann equilibrium between excited levels established after the absorption process, it is independent of how these levels were initially exvited. Excitation can, therefore, be effected by absorption of light of any photon energy higher than that of level 84.

Since the temperature variation of the luminescence decay time $\tau$ is independent of whether optical excitation occurs from the lowest occupied sublevel of the ground electronic level or from a vibrationally excited sublevel (vibronic level), a vibronic material having two emissive levels in thermal equilibrium provides at least two independent phenomena useful for measuring temperature: (a) the temperature-dependent absorption process discussed with reference to FIG. 2, and (b) the processes discussed in this section.

Self-checking operation of optical temperature sensors

A considerable amount of time is spent in industry checking the accuracy of thermometric devices. Checking procedures usually require the use of an auxiliary calibrated thermometric device. The methods and materials disclosed herein permit automatic independent checks of the accuracy of measurements carried out according to any of the methods disclosed hereinbefore, without the need of any additional sensor, light source, photodetector or optical component. For instance, many vibronic luminescent materials characterized by a temperature-dependent light absorption are also characterized by a temperature-dependent luminescence decay time, or a temperature-dependent luminescence spectral distribution, neither of which depend on on the occupancy number of any vibronic level. Therefore one can, by simply adding inexpensive electronic components, compare a temperature reading operationally determined by the occupancy number of a vibronic level of the sensor to the temperature reading from the same sensor determined from either its luminescence decay time or its luminescence spectral distribution. The measurements being carried out simultaneously or sequentially by means known in the art.

A simple device for the optical measurement of temperature according to the methods of this invention is shown schematically in FIG. 5, wherein the temperature sensor 100 consists of one of the luminescent materials disclosed herein, the absorption coefficient of which varies as a known function of temperature when excited with light of photon energy lower than the energy $E_s$ of the excited emissive level, and the luminescent centers of which have a luminescence decay time $\tau$ of the order of $10^{-5}$ seconds, or longer. Sensor 100 is illuminated with light of said photon energy lower than $E_s$, generated from light source 120, said light source being preferably, but not limited to, a light-emitting diode (LED) or a diode laser. The light source is pulsed or AC-modulated by the AC or pulse power supply 130, so that its light intensity decays repetitively in a time much shorter than $\tau$. The excitation light from 120 is directed to sensor 100 via the fiber optics light guide 160. The excitation light transmitted by, and the luminescence light emitted by sensor 100 are both carried, via the fiber optics light guide 170, to photodetector 240, and the electrical signals generated therein are separated by the electrical frequency filters 250 and 270. Filter 250 transmits the electrical signal of the transmitted excitation light, whereas filter 270 transmits the electrical signal produced by the sensor luminescence. The ratio of these signals, measured by the electronic divider 300, is an indicator of the sensor temperature, which is displayed on the display device 320. It should be obvious that a similar device can be used when the sensor contains two kinds of luminescent centers, A and B as defined above, the luminescence decay times of which are very different from each other.

A parallel arrangement of electrical frequency filters is useful for measuring a temperature-dependent luminescence decay time. The filters are tuned, respectively, to the time frequencies corresponding to the upper and lower limits of the decay time within the temperature range of operation of the device. The relative fractions of the electrical signals transmitted by the filters is an indicator of the luminescence decay time and, hence, of the sensor temperature. Thus, by adding another electrical frequency filter to the device shown in FIG. 5, one can measure both the temperature-dependent light absorption (and luminescence intensity) of the sensor and its temperature-dependent luminescence decay time. Since both parameters are operationally independent of each other, such a simple device can check its own accuracy by comparing the readings obtained from both measurements.

Examples of applications

Suppose that we desire an intrinsically safe thermometer which can be used in flammable or explosive atmospheres Suppose that we desire a thermometer which could be used safely in potentially flammable or explosive atmospheres, without danger of accidentally igniting a combustible mixture. We require, (a) a range of application from $-200°$ C. to $450°$ C. that is, a range of 650 degrees Celsius;

(b) a temperature coefficient of change no smaller than one percent per degree Celsius, in at least one mode of operator, over the whole temperature range of operation; and (c) a luminescence quantum efficiency no lower than 0.5 (in order to obtain large signals) over the whole temperature range.

To begin with, we note that none of the methods of the prior art using luminescent probes can satisfy a single one of these requirements. However, with the teachings of this invention one can satisfy all of them with a single probe. We use the following approach:

The self-checking capability indicates a probe material which can be operated both according to the scheme described with reference to FIGS. 2 or 3, that is, the 'vibronic' mode of operation according to equation (4), and the luminescence decay time mode according to the scheme of FIG. 4. This suggests chromium-(III)-doped inorganic crystals with a Boltzmann equilibrium between two excited emissive levels. These levels are the $^2E$ and $^4T_2$ levels of Cr(III), corresponding to levels 84 and 82 of FIG. 4, respectively. A survey of known materials indicates that emerald (chromium-doped beryl) meets this requirement. In addition, emerald is known to have a high luminescence quantum efficiency, higher than 0.5° at 450° C. and even higher at lower temperatures, Emerald has, approximately, the following values for the parameters of equation (9): $E' \approx 388$ cm$^{-1}$; $k_r \approx 676$ sec$^{-1}$, and $k_r' \approx 8.5 \times 10^4$ sec$^{-1}$ (W. H. Fonger and C. W. Struck, *Physical Review B*, pp b 3251ff, May 1975).

In the decay time mode of operation, one can use an emerald probe in a device as described with reference to FIG. 5. The luminescence of emerald is excited with light pulses with a wavelength of 720 nm of shorter, and a pulse duration of about 10 microseconds ($10^{-5}$ sec). This probe is being used in the cryogenic region comprising the temperature region of liquefied natural gas (LNG), a technologically important region. LNG boils at 112 kelvins ($-161°$ C.). Using equation (9) and the listed values of E', $k_r$ and $k_r'$, we calculate a luminescence decay time $\tau$ of $7.95 \times 10^{-4}$ seconds, which essentially corresponds to the experimentally observed value. An increase in temperature of one degree Celsius causes a decrease in $\tau$ of 2 percent, to $7.79 \times 10^{-4}$ sec. This is a relatively large temperature coefficient of change. Therefore, by measuring $\tau$ at any unknown temperature one readily measures said temperature with high accuracy.

The device can also be operated in the 'vibronic' mode. The same reference by Fonger and Struck indicates that energy level $^4T_2$ has an energy $E_s$ of about 14,090 cm$^{-1}$. Excitation of this level can be effected from a vibrational sublevel of the ground electronic state according to the vibronic mode of FIG. 3. One can choose, for example, an $E_v$ value of 200 cm$^{-1}$, suitable for the LNG range, by using an illuminating wavelength of 720 nanometers (nm). $E_v$ is given by the relation $$E_v = E_s - (hc/\lambda e)$$

where h is Planck's constant,
c is the velocity of light in a vacuum, and $\lambda_e$ is the wavelength of the illuminating light.

In a preferred embodiment the optical path length of the emerald probe and the chromium concentration are chosen so that the optical density of the probe at the temperature of 112 kelvins is not much greater than about 0.02. Then, with a device such as the one described in FIG. 5, one measures the relative intensities of the light transmitted and the luminescence light emitted by the probe (sensor). The ratio R of these intensities is a unique function of temperature, with the luminescence intensity varying with temperature according to equation (4). The intensity of the transmitted light is proportional to $(1-\alpha_\nu)$, where $\alpha_\nu$ is the temperature-dependent fraction of the illuminating light intensity which is absorbed by the emerald sensor. The value of I, the luminescence intensity, has a temperature coefficient given by equation (5). At the reference temperature of 112 kelvins, the boiling point of LNG, the temperature coefficient of I is about 2.3 percent per degree Celsius (or, per kelvin).

The above device can also be operated in the self-checking mode. This is done by measuring both the value of R, obtained at an excitation wavelength of 720 nm, and the luminescence decay time $\tau$. Each of these parameters provides an independent temperature indicator and, except in case of device malfunction, the temperature reading obtained from R should be the same as that obtained from $\tau$ at the same temperature. Any discrepancy will indicate malfunction of the device. Thus, the device is self-checking.

The emerald probe can be used at higher temperatures in either of the two measurment modes, and in the self-checking mode. The rate of change of $\tau$ with temperature is lower at temperatures higher than about 250 kelvins, but still high enough for most applications. The upper limit of operation of the emerald probe is about 800 kelvins.

All optical radiometric temperature measurements

Line-of-sight infrared pyrometry and infrared thermography are widely used for non-contact temperature measurements, and the advent of microprocessors has resulted in sophisticated, accurate and portable instruments for these applications. Virtually all of these instruments use electrical sensors. A small but increasing number of applications require pyrometric or thermographic measurements in electrically hostile environments, for instance in the presence of strong radiofrequency (RF) fields. All-optical radiometers or thermographs are useful under these conditions, as they are immune to RF and other electrical interference. Infrared sensors made of luminescent films are attractive elements for making such devices. Such films must have a high luminescence efficiency, a high temperature coefficient of luminescence intensity and a low thermal mass. The last requirement mandates a high absorption coefficient for the luminescence excitation radiation. Of the materials disclosed above, europium-doped terbium chelates and luminescent semiconductors meet these requirements. A further need for some applications is the ability to both excite the sensor luminescence and to transmit the infrared-generated signals over long distances. Thin luminescent films of semiconductors having a temperature-dependent absorption edge meet this requirement.

All-optical radiometers and thermal-imaging films offer the possibility of positioning a small detector head in optical contact with a fiber optic cable at locations not accesible to conventional radiometric devices.

Some changes may be made in the foregoing disclosure without departing from the scope of the invention herein involved. Therefore, all matter contained in the above description and depicted in the disclosed embodiments and drawings should be construed in an illustrative and not in a limiting case.

I claim:

1. A method for measuring the temperature of an object or environment, comprising the steps of:
    (a) placing a temperature sensor in a heat flow relationship with said object or environment, said sensor consisting of a material containing luminescence centers characterized by absorbing, when illuminated with light within a defined spectral region for said luminescent material, a fraction of the intensity of said illuminating light incident on said sensor, said fraction varying as a known function of the temperature of said sensor, said sensor emitting luminescence light with an intensity that varies as a known function of the intensity of said absorbed light,
    (b) illuminating said sensor with excitation light within said defined spectral region, thereby causing the absorption of said temperature-dependent fraction of the intensity of said light, the transmission of the non-absorbed fraction of the intensity of said light, and the emission of luminescence light within a spectral region characteristic of said luminescent centers, the intensity of said luminescence light being related to said temperature-dependent absorbed fraction of the intensity of the excitation light,
    (c) directing said luminescence light from said sensor to a photo-detector, and
    (d) measuring the intensity of said luminescence light, said intensity being an indicator of the temperature of said sensor, and related to the temperature of said object or environment.

2. A method as defined by claim 1 and additionally comprising the steps of:
    (a) measuring, by means of a photo-detector, the fraction of the intensity of said excitation light which is transmitted by said sensor, and
    (b) measuring the relative intensities of the luminescence light emitted by said sensor and the excitation light transmitted by said sensor, said relative intensities being an indicator of the sensor temperature, essentially independent of any fluctuations of the intensity of said excitation light.

3. A method as defined by claim 2 wherein the intensity of said excitation light varies in an oscillatory or pulsating manner with a decay time much shorter than the decay time of the sensor luminescence, thus generating a luminescence from the sensor which varies more slowly with time than said excitation light transmitted by the sensor, and wherein both said luminescence light and said transmitted excitation light are directed to and detected by a single photo-detector, this method additionally comprising the steps of:
    (a) separating the electrical signals produced at the photo-detector by said excitation light transmitted by the sensor and by said luminescence light, and
    (b) measuring the relative values of said separated electrical signals, said relative values representing the relative intensities of the excitation light transmitted and the luminescence light emitted by said sensor, said relative intensities being an indicator of the sensor temperature.

4. A method as defined by claim 1 wherein said luminescent material contains, in addition to said luminescent centers characterized by a temperature-dependent absorption of light, designated in this claim as A centers, a second kind of luminescent centers, designated in this claim as B centers, the absorption coefficient of which is approximately independent of temperature within the temperature range being measured, when illuminated as recited in subparagraph (b) of claim 1, the method of this claim additionally comprising the steps of:
(a) measuring the intensity of the luminescence emitted by the B centers, and
(b) measuring the relative intensities of the luminescence lights emitted by the A centers and the B centers, said relative intensities being an indicator of the sensor temperature.

5. A method as defined by claim 4, wherein the intensity of said excitation light varies in an oscillatory or pulsating manner with a decay time much shorter than the luminescence decay time of one, and only one of said two kinds of luminescent centers, thus generating a luminescence emission from one of said two kinds of luminescent centers the intensity of which has a time-dependence different from that of the luminescence emission from the other centers, and wherein the luminescence emissions from both said A and said B centers are directed to and detected by a single photo-detector, this method additionally comprising the steps of:
(a) separating, by means of known electrical timing techniques, the electrical signals produced at the photo-detector by the luminescence emissions from said A centers and from said B centers, and
(b) measuring the relative intensities of said separated electrical signals, said relative intensities being an indicator of the sensor temperature.

6. A method as defined by claim 2 wherein the excitation light is carried to the luminescent sensor by means of at least one optical fiber, the generated luminescence is directed to its photo-detector by means of at least one optical fiber, and the light transmitted through the luminescent material is directed to its photo-detector by means of at least one optical fiber.

7. A method as claimed in claim 1 wherein said luminescent centers are additionally characterized by emitting, when excited with light of any wavelength within a defined spectral region for said sensor, including but not limited to the spectral region recited in claim 1, luminescence lights from two excited energy levels, the relative intensities of which are a known monotonic function of temperature, the luminescence intensity from the upper of said levels increasing with an increase in temperature within the temperature range being measured, said intensity increase producing a decrease of the decay time of the luminescence emitted from said levels, and wherein the intensity of the excitation light is made to vary in an oscillatory or pulsating manner with a decay time shorter than the decay time of the sensor luminescence emitted from said two energy levels, the method additionally comprising the steps of:
(a) measuring the decay time of the sensor luminescence emitted by said two excited levels, said decay time being an additional and independent indicator of the sensor temperature, and
(b) comparing the temperature reading obtained from the intensity of the luminescence light generated by the absorption of said temperature-dependent fraction of the intensity of the illuminating light to the temperature reading obtained from said decay time of the sensor luminescence.

8. A method as defined by claim 1 wherein the excitation light is carried to the luminescent sensor by means of at least one optical fiber, and wherein the generated luminescence is directed to the photo-detector by means of at least one optical fiber.

9. A method as defined by claim 8 wherein the luminescent material is a vibronic material characterized by an optical absorption coefficient which varies as a known function of the occupancy number of at least one vibronic level.

10. A method as defined by claim 8 wherein the luminescent material is a semiconductor with a temperature-dependent absorption edge.

11. A method as defined by claim 8 wherein the luminescent material is a glass doped with a lanthanide ion having an electronic energy level which is thermally excited at the temperature being measured, the occupancy number of said electronic level increasing with an increase in temperature.

12. A method for measuring the temperature of an object or environment comprising the steps of:
(a) placing a temperature sensor in a heat flow relationship with said object or environment, said sensor consisting of a material containing luminescent centers characterized by emitting, when excited with light of any wavelength within a defined spectral region for said sensor, luminescence lights from two excited energy levels, the relative intensities of which are a known monotonic function of temperature, the luminescence intensity from the higher of said levels increasing with an increase in temperature within the temperature range being measured, said intensity increase producing a decrease of the decay time of the total luminescence from the sensor,
(b) exciting the luminescence of said sensor with light within said defined spectral region, thereby causing luminescence emissions from said two energy levels, the relative intensities of which are a know function of temperature,
(c) directing the luminescence lights emitted by said sensor to a photo-detection station, and
(d) measuring the relative intensities of said luminescence emissions from said two energy levels, said relative intensities being an indicator of the sensor temperature.

13. A method as defined by claim 12 wherein the intensity of said excitation light is made to vary in an oscillatory or pulsating manner with a decay time shorter than the decay time of the sensor luminescence emitted from said two energy levels, and wherein the measurement of the relative intensities of said luminescence emissions from said two energy levels is effected by measuring said luminescence decay time, said decay time being an indicator of the sensor temperature.

14. A temperature probe consisting of a solid luminescent material, said probe material containing therein:
(a) luminescent centers, designated herein as A centers, characterized by absorbing, when exposed to light within a defined spectral region, a fraction of the intensity of said light incident on said material, said fraction varying as a known function of the temperature of said material, and by emitting luminescence light with an intensity that varies as a known function of the intensity of said absorbed light, and (b) luminescent centers, designated herein as B centers characterized by an absorption coefficient and luminescence intensity which are approximately independent of temperature, within the temperature range being measured, when excited with light within said defined spectral region, the luminescence of these centers being emitted in a spectral region different from that of the luminescence of the A centers, the concentration of the B centers being such as to absorb only a fraction of said incident light within said defined spectral region.

15. A device for the optical measurement of temperature comprising:

(a) a sensor consisting of a luminescent material containing luminescent centers characterized by absorbing, when illuminated with light within a defined spectral region for said luminescent material, a fraction of the intensity of said illuminating light incident on said sensor, said fraction varying as a known function of the temperature of said sensor, said sensor emitting luminescence light with an intensity that varies as a known function of the intensity of said absorbed light, (b) a source of luminescence excitation light within said defined spectral region, (c) fiber optic means for directing said excitation light to said sensor, thereby generating luminescence emission, (d) fiber optic means for directing the excitation light transmitted by said sensor and the luminescence light emitted by said sensor to a photo-detection station, (e) a photo-detection station for measuring the intensity of said excitation light transmitted by said sensor and the intensity of said luminescence light emitted by said sensor, and (f) means for measuring the relative values of the electrical signals generated at said photo-detection station by said excitation light transmitted by said sensor and by said luminescence light emitted by said sensor, said relative values being an indicator of the sensor temperature.

16. A device as defined by claim 15 and also comprising optical filter means for separating said excitation light transmitted by said sensor from said luminescence light emitted by said sensor.

17. A device as defined by claim 15 wherein said excitation light source is characterized by producing a recurrent light intensity which decays in a period much shorter than the decay time of the sensor luminescence, and wherein said luminescence light emitted by said sensor and said excitation light transmitted by said sensor are both directed to a single photo-detector, and also comprising electrical frequency filter means for separating said electrical signal generated by said excitation light transmitted by said sensor from said electrical signal generated by said luminescence light emitted by said sensor.

18. A device as claimed in claim 15 wherein said luminescent centers are additionally characterized by emitting, when excited with light of any wavelength within a defined spectral region for said sensor, including but not limited to the spectral region recited in claim 15, luminescence lights from two excited energy levels, the relative intensities of which are a known monotonic function of temperature, the luminescence intensity from the upper of said levels increasing with an increase in temperature within the temperature range being measured, said intensity increase producing a decrease in the decay time of the luminescence emitted from said energy levels, and wherein the intensity of the excitation light is made to vary in an oscillatory or pulsating manner with a decay time shorter than the decay time of the sensor luminescence, emitted from said two excited energy levels, the device additionally comprising:

(a) means for measuring the decay time of the sensor luminecence emitted by said two excited energy levels, said decay time being an additional and independent indicator of the sensor temperature, and (b) electronic means for comparing the temperature reading obtained from the intensity of the luminescence light generated by the absorption of said temperature-dependent fraction of the intensity of the illuminating light to the temperature reading obtained from said decay time of the sensor luminescence.

19. A device for the optical measurement of temperature comprising:

(a) a temperature sensor consisting of a luminescent material containing luminescent centers characterized by emitting, when excited with light within a defined spectral region, luminescence light from two excited energy levels, the luminescence intensity from the higher of said levels increasing with an increase in temperature, said luminescent centers also characterized by a luminescence decay time which decreases in a known manner with an increase in temperature, (b) a source of repetitive pulses of luminescence excitation light, the intensity of which decays in a time much shorter than the decay time of the luminescence emitted by said sensor, (c) fiber optic means for directing said pulses of luminescence excitation light to said sensor, (d) fiber optics means for directing said luminescence light emitted from said two excited levels emissive excited levels of said sensor to a single photo-detector, and (e) a photo-detector and associated electronic means for measuring the decay time of said luminescence light, said decay time being an indicator of the sensor temperature.

20. A device for the optical measurement of temperature comprising:

(a) a temperature sensor consisting of a solid containing two kinds of luminescent centers designated herein as A centers and B centers, said A centers characterized by an absorption coefficient which varies as a known function of temperature when excited with light within a defined spectral region, and said B centers characterized by an absorption coefficient and a luminescence intensity which are approximately independent of temperature within the temperature range being measured, when excited with light within said defined spectral region, (b) a source of luminescence excitation light within said defined spectral region, (c) fiber optics means for directing said excitation light to said sensor, (d) fiber optics means for directing the luminescence light emitted by said sensor to a photo-detection station, and (e) a photo-detection station and associated electronic components for measuring the intensities of the luminescence emitted from each of said two kinds of luminescent centers, the ratio of said luminescence intensities being an indicator of the sensor temperature.

21. A device as described in claim 20 wherein the two kinds of luminescent centers in said temperature sensor emit luminescence in different, separable spectral regions, and wherein
(a) said means for directing the luminescence emitted by the sensor to the photo-detection system comprises at least one optical filter for separating the luminescence components emitted by each of said two kinds of luminescent centers, and means for directing each separated luminescence component to a separate photo-detector, and
(b) the photo-detector system comprises two photo-detectors with their associated electronic components, each photo-detector being used for measuring the intensity of each of said separated luminescence components.

22. A device as defined by claim 20 wherein said photo-detection station comprises a single photo-detector with its associated electronic components, said device also comprising:
(a) means for time-modulating the light output of said source of luminescence excitation light to make the intensity of said excitation light vary in an oscillating or pulsating manner with a decay time much shorter than the luminescence decay time from one, and only one, of said two kinds of luminescent centers, and
(b) electrical frequency filters for separating the electrical signals generated at said photo-detector by the luminescence emissions from each of said two kinds of luminescent centers, said separated signals being related to the intensities of the luminescence emissions from each of said two kinds of luminescent centers.

* * * * *

UNITED STATES PATENT AND TRADEMARK OFFICE
CERTIFICATE OF CORRECTION

PATENT NO. : 4,708,494

DATED : November 24, 1987

INVENTOR(S) : Marcos Y. Kleinerman (Marcos Kleinerman)

It is certified that error appears in the above-identified patent and that said Letters Patent is hereby corrected as shown below:

Column 1, line 62, "uses" should be --used--;

Column 3, line 15, the word --chelates-- should be inserted between "terbium" and "require";

Column 6, line 7, "measure" should be --measured--;

Column 6, lines 63 and 64, "material" should be --materials--;

Column 9, line 43, "increases" should be --decreases--;

Column 10, line 37, "europium(KII)" should be --europium(III)--;

Column 12, line 56, "intefrated" should be --integrated--;

Column 13, line 54, "$k_r$ and $k_r'$" should be --$k_r'$ and $k_r$--;

Column 14, after line 4, the numerator "$[1 - \exp(-E'/kT)]$" in equation (9) should be --$[1 + \exp(-E'/kT)]$--;

Column 14, line 41, "exvited" should be --excited--;

Column 16, line 33, "676" should be --700--;

Column 16, line 39, "720" should be --680--;

Column 16, line 49, delete ", to $7.79 \times 10^{-4}$ sec";

UNITED STATES PATENT AND TRADEMARK OFFICE
CERTIFICATE OF CORRECTION

PATENT NO. : 4,708,494

DATED : November 24, 1987

INVENTOR(S) : Marcos Y. Kleinerman (Marcos Kleinerman)

It is certified that error appears in the above-identified patent and that said Letters Patent is hereby corrected as shown below:

Column 16, line 57, "14,090" should be --14,990--;

Column 16, line 62, "720" should be --676--; and

Column 17, line 23, "720" should be --676--.

Signed and Sealed this

Twenty-seventh Day of September, 1988

Attest:

DONALD J. QUIGG

*Attesting Officer*     *Commissioner of Patents and Trademarks*

UNITED STATES PATENT AND TRADEMARK OFFICE
CERTIFICATE OF CORRECTION

PATENT NO. : 4,708,494

DATED : November 24, 1987

INVENTOR(S) : Marcos Kleinerman

It is certified that error appears in the above-identified patent and that said Letters Patent is hereby corrected as shown below:

Column 22, line 42, delete "levels".

Column 22, line 43, delete "excited".

Signed and Sealed this

Ninth Day of January, 1990

*Attest:*

JEFFREY M. SAMUELS

*Attesting Officer*     Acting Commissioner of Patents and Trademarks

UNITED STATES PATENT AND TRADEMARK OFFICE
CERTIFICATE OF CORRECTION

PATENT NO. : 4,708,494

DATED : November 24, 1987

INVENTOR(S) : Marcos Y. Kleinerman ( Marcos Kleinerman)

It is certified that error appears in the above-identified patent and that said Letters Patent is hereby corrected as shown below:

Column 22, line 41, delete "levels";
Column 22, line 42, delete "excited".

Signed and Sealed this

Eleventh Day of February, 1992

Attest:

HARRY F. MANBECK, JR.

*Attesting Officer*　　　　　*Commissioner of Patents and Trademarks*